United States Patent [19]

Presby

[11] 4,042,723
[45] Aug. 16, 1977

[54] METHOD FOR MONITORING THE PROPERTIES OF PLASTIC COATINGS ON OPTICAL FIBERS

[75] Inventor: Herman Melvin Presby, Highland Park, N.J.

[73] Assignee: Bell Telephone Laboratories, Incorporated, Murray Hill, N.J.

[21] Appl. No.: 685,527

[22] Filed: May 12, 1976

[51] Int. Cl.$^2$ .......................... G01B 9/02; B32B 17/04
[52] U.S. Cl. ........................................ 427/8; 356/107; 356/108; 356/109; 427/10
[58] Field of Search ...................... 427/8, 10; 356/107, 356/108, 109

[56] References Cited

U.S. PATENT DOCUMENTS 3,879,128   4/1975   Presby ........................... 356/107 X

OTHER PUBLICATIONS

Presby et al., Applied Optics, vol. 13, No. 12, pp. 2882-2885, (Dec. 1974).

*Primary Examiner*—James R. Hoffman
*Attorney, Agent, or Firm*—Stephen M. Gurey

[57] ABSTRACT

The concentricity and uniformity of a plastic coating as it is applied to an optical fiber are monitored by comparing the backscattered light patterns generated by two mutually perpendicular light beams incident upon the coated fiber.

10 Claims, 23 Drawing Figures

METHOD FOR MONITORING THE PROPERTIES OF PLASTIC COATINGS ON OPTICAL FIBERS

BACKGROUND OF THE INVENTION

This invention relates to optical fibers and, more particularly, to a method for optically monitoring the properties of plastic coatings as they are applied to optical fibers.

Plastic coatings that are applied to optical fibers serve multiple purposes. When applied as an overcoat to glass-clad optical fibers, they serve to reduce microbending loss, maintain the pristine strength of the fibers and provide for abrasion and mechanical protection of the fibers during cable manufacturing processes. In addition, the plastic coated fiber may decrease crosstalk between optical fibers and improve the long term stability of fibers in an uncontrolled environment. The plastic coating can also be directly used as the cladding for fused silica cores since the refractive index of many polymer materials is less than that of fused silica.

For optimum performance the coating must be applied uniformly and concentrically around the fiber. This is necessary for routine handling and splicing of the fibers as well as for optimum strength and transmission characteristics.

The coatings which include such materials as silicon, epoxy-acrylates, tetrafluoroethylene, perfluoro-vinylmethyl ether, perfluoronated-ethylenepropylene, and ethylene-vinyl-acetate copolymer, are applied to fibers by various methods. Prior art techniques for examining the concentricity of coatings once they are produced require the microscopic examination of the fiber after a run has been processed. In addition to being time-consuming and destructive, this prior art procedure may not detect beading or gross nonuniformities which could seriously impair the transmission characteristics of the fiber. More importantly, real time information to enable the fabricator to make corrections, evaluate various applicators or stop the process completely is not available as the coating is being applied.

In U.S. Pat. No. 3,879,128, issued Apr. 22, 1975, to the present inventor, the evaluation of various parameters of an optical fiber by examining the backscattered light produced in response to an incident beam is disclosed. The disclosed method, however, cannot determine the concentricity and uniformity of application of plastic coatings on an optical fiber.

SUMMARY OF THE INVENTION

The object of the present invention is to monitor the properties of plastic coatings as they are applied to optical fibers.

In accordance with the present invention the properties of substantially transparent plastic coatings which have been applied to optical fibers are monitored by comparing the backscattered light patterns generated in response to two mutually orthogonal light beams incident upon the coated fiber. In particular, the concentricity of a fiber within a plastic coating is determined by comparing the location of unique intensity peaks in each backscattered light pattern. In a particular embodiment of the present invention each backscattered light pattern is converted into an electrical signal, from which such comparisons are made. Such a comparison generates a feedback signal that controls the application process to maintain proper positioning of the coating applicator around the fiber.

A feature of the present invention is that the coating may be maintained at a predetermined thickness by monitoring the backscattered light patterns for the disappearance of particular intensity peaks.

DETAILED DESCRIPTION

Figure 1:
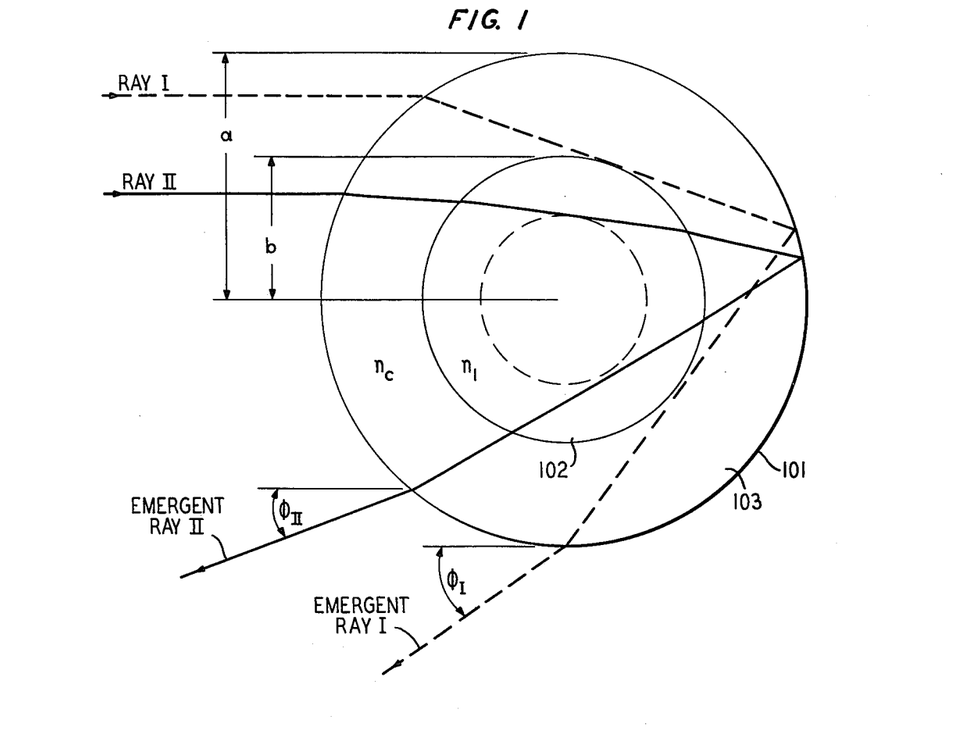
FIG. 1 is a cross-sectional view of a plastic coated fiber which illustrates rays of light incident thereon.

With reference to FIG. 1, a beam of light is shown incident upon a cross-sectional area of a plastic coated optical fiber 101 having a radius $a$. As described hereinabove, the interior fiber 102 having a radius $b$, can either be a fused silica fiber core, or the interior fiber 102 can include both a core and a cladding. In the first case, the plastic coating 103 surrounding the core acts as both in the cladding and as a protective sheath and must have an index of refraction less than the index of refraction of the core. In the latter case, plastic coating 103 serves merely as a protective sheath for the fiber. FIG. 1 thus illustrates the cross-section of the coated fiber as having either two or three layers. The incident light beam includes parallel rays such as illustrated by Ray I, which are refracted at the air coating interface, traverse the coating, and are then reflected at the coating-air interface and exit the coating. The angle of minimum deviation $\phi_i$ that emergent Ray I makes with its incident direction is given by:

$$\phi_I = \tag{1}$$

$$4\arcsin\left[\frac{2}{n_c\sqrt{3}}\left(1 - \frac{n_c^2}{4}\right)^{\frac{1}{2}}\right] - 2\arcsin\left[\frac{2}{\sqrt{3}}\left(1 - \frac{n_c^2}{4}\right)^{\frac{1}{2}}\right]$$

where $n_c$ is the refractive index of the plastic coating 103. The incident light beam also includes rays such as illustrated Ray II which are refracted by the coating, traverse the fiber, emerge into the coating again and are reflected by the coating-air interface. These rays then enter the fiber and emerge into the coating and from there leave the fiber. A geometric-optical analysis readily shows the angle of minimum deviation $\phi_{II}$ of these emergent rays to be a function of several angles and of the indices of refraction of the coating and the fiber. Such an analysis is presented in "Refractive Index and Diameter Determination of Step Index Optical Fibers and Preforms", by H. M. Presby and D. Marcuse, *Applied Optics*, Vol. 13, No. 12, December 1974, pp 2882–2885.

The parallel rays incident upon the coated fiber which traverse only the plastic coating, such as Ray I, or which traverse both the coating and the fiber, such as Ray II, create a backscattered light pattern, which can be observed on an opaque viewing screen perpendicular to the incident beam. For our purposes, the backscattered light pattern is characterized by two pairs of intensity peaks. The spatial locations of the first pair of intensity peaks are determined from the angle of minimum deviation $\phi_I$ for the incident rays which traverse only the coating. The spatial locations of the second pair of intensity peaks are determined from the angle of minimum deviation $\phi_{II}$ for the incident rays that traverse both the coating and the fiber.

It has been found that the spatial location of the intensity peaks in the backscattered light pattern varies as a nonconcentric plastic coated fiber is rotated within an incident beam. The concentricity of a section of coated fiber can thus be monitored by noting variations in the locations of the intensity peaks in the backscattered light pattern as the fiber is rotated. It has been further found that the concentricity of a fiber within a plastic coating can be determined with a finite number of comparisons of the locations of the intensity peaks in the backscattered patterns. In particular, by comparing the backscattered light pattern generated for two mutually perpendicular fiber orientations, the concentricity of the fiber section upon which the beam impinges is readily ascertained. As an alternative to rotating the coated fiber within an incident beam, two beams which are incident upon the same section of coated fiber may be employed to monitor the fiber.

Apparatus will be described in detail hereinafter which monitors the concentricity of a coated fiber as the coating is applied by comparing the spatial positions of the intensity peaks in the backscattered light patterns generated in response to two mutually perpendicular beams incident upon the fiber. In addition, the fiber is monitored for nonuniformities and irregularities in the plastic coating by observing the backscattered light patterns.

As discussed hereinabove, the rays incident on the coated fiber either traverse only the plastic coating 103, such as Ray I, or traverse both the coating 103 and the fiber 102, such as Ray II. It can be readily shown, however, that when the thickness of the plastic coating is less than a critical thickness all incident rays will traverse both the coating and the fiber. In particular, when the ratio of radius $a$ of the coated fiber and radius $b$ of the fiber is less than the index of refraction of the plastic coating $n_c$, all incident rays traverse the coating and the fiber. There is thus only one ray of minimum deviation and only one pair of intensity peaks is present in the backscattered light patterns. Since the fiber has a known fixed radius, and the coating material has a known fixed index of the refraction, the radius of the coated fiber can be uniformly maintained at $bn_c$ by monitoring the backscattered light patterns for the disappearance of the second pair of intensity peaks. The coating thickness can thus be maintained at $b(n_c - 1)$. Apparatus will be described hereinafter which automatically monitors the backscattered light patterns for the disappearance of these intensity peaks and thus controls the application process to uniformly maintain coating thickness at this predetermined value.

Figure 2:
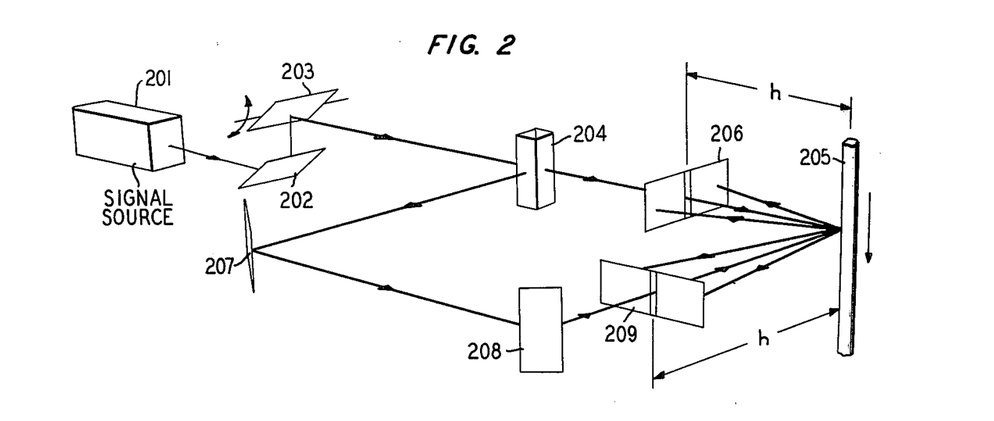
FIG. 2 shows apparatus for monitoring the properties of a plastic coated fiber in accordance with the principles of the present invention.

FIG. 2 shows an arrangement for observing the backscattered light patterns in response to two light beams incident upon a substantially transparent plastic coated optical fiber. A signal source 201, such as a CW He-Ne laser, generates a narrowband light beam which is incident upon a mirror 202. The light beam is reflected onto an oscillating mirror 203 which oscillates back and forth to transform the beam into a line of light energy. A beam splitter 204 divides the line of light energy reflected by oscillating mirror 203 into two portions. A portion of the divided beam is transmitted directly onto a segment of the fiber 205 through a slit in an opaque observation screen 206. Observation screen 206 is perpendicularly disposed in the path of light at a distance $h$ from the fiber to be monitored. The other portion of the beam incident upon beam splitter 204 is reflected by plane mirrors 207 and 208 and transmitted through a slit in an observation screen 209 so as to impinge upon the same segment of fiber 205 at right angles to the portion of the beam directly incident upon the fiber. Observation screen 209 is also perpendicularly disposed in the path of light energy transmitted therethrough and is also located a distance $h$ from the fiber. Each incident beam is refracted through the substantially transparent plastic coating and the interior fiber and reflected at the coating-air interface to form backscattered light patterns which are observable on observation screens 206 and 209.

By comparing the locations of the intensity peaks in the backscattered light patterns on observation screens 206 and 209, the concentricity of the fiber within the plastic coating and the uniformity of coating application of the fiber section upon which the two incident light beams impinge is determined. Therefore, by monitoring these two observation screens as a fiber is drawn through the incident light beams, the properties of the plastic coating are readily determined. As will be described in detail hereinafter, the comparison of intensity peaks can be automatically performed to generate a feedback signal which controls the plastic coating applicator. Proper concentricity and uniformity of application is thus maintained throughout the coating application process.

Figure 3A:
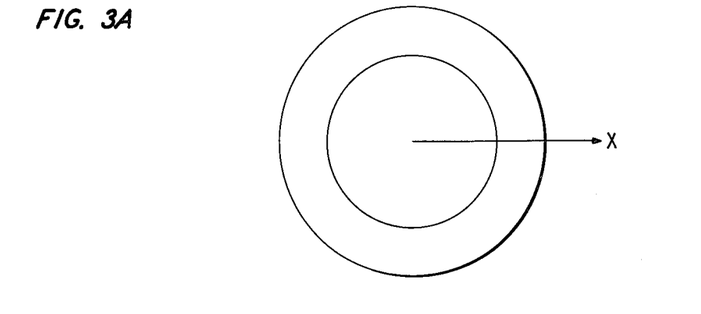
FIG. 3A is a cross-sectional view of a concentric plastic coated fiber.
Figure 3B:
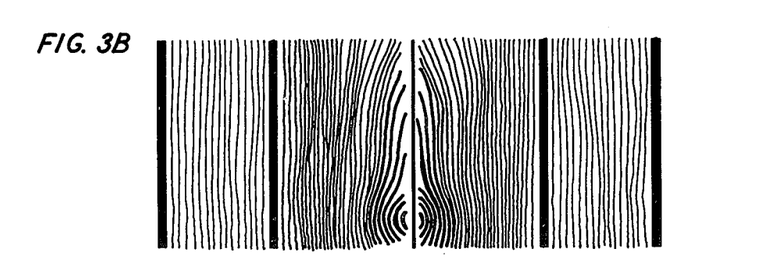
FIGS. 3B and 3C show the backscattered light patterns generated in response to light beams incident upon the fiber in FIG. 3A.
Figure 3C:
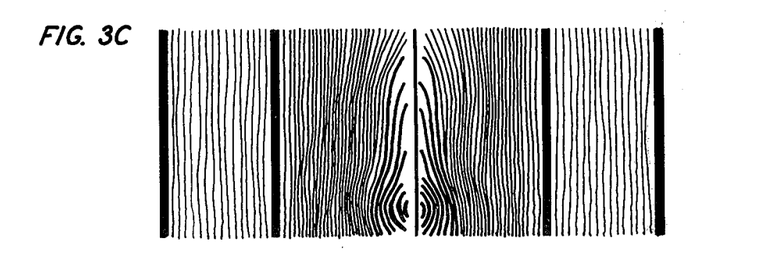

FIG. 3A illustrates a cross-section of a concentrically coated fiber. FIG. 3B is the backscattered light pattern generated in response to an incident light beam making an angle of zero degrees with the X axis of the fiber in FIG. 3A. FIG. 3C is the backscattered light pattern generated in response to a light beam making an angle of 90 degrees with the X axis of the fiber in FIG. 3A. As can be noted, the intensity peaks in FIGS. 3B and 3C are located at correspondingly similar coordinates thus indicating concentricity of the fiber within the coating.

Figure 4A:
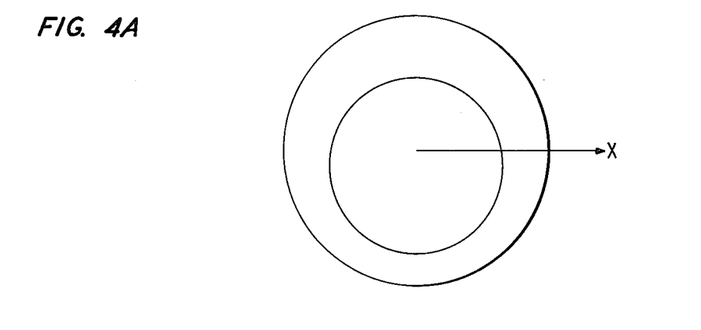
FIG. 4A is a cross-sectional view of a non-concentrically coated fiber.
Figure 4B:
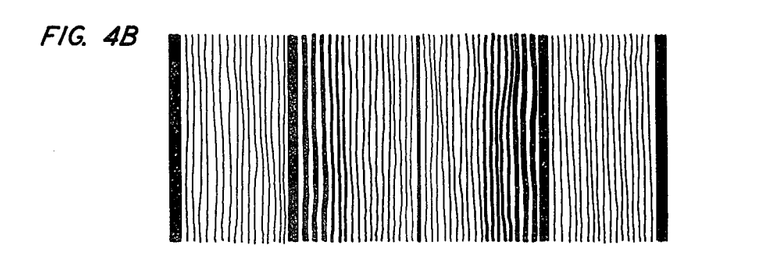
FIGS. 4B and 4C show the backscattered light pattern generated in response to light beams incident upon the fiber of FIG. 4A.
Figure 4C:
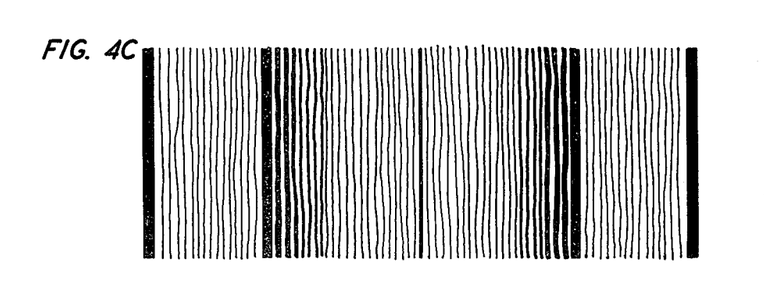

FIG. 4A illustrates a cross-section of a nonconcentric plastic coated fiber. As can be observed in the backscattered light patterns in FIGS. 4B and 4C, respectively, the coordinates of the intensity peaks are not aligned. This indicates, therefore, the nonconcentricity of the section of the fiber upon which the incident light beams have impinged.

Figure 5A:
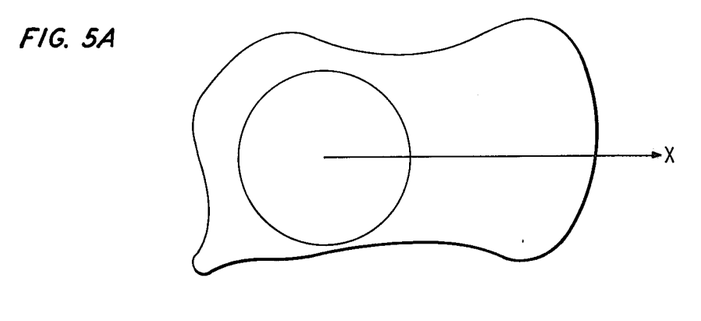
FIG. 5A is a cross-sectional view of a deformed plastic coated fiber.
Figure 5B:
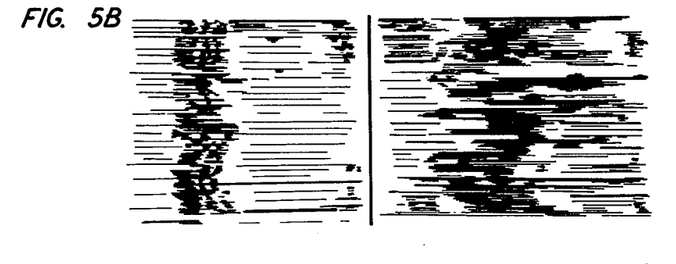
FIGS. 5B and 5C show the backscattered light patterns generated in response to light beams incident upon the deformed fiber of FIG. 5A.
Figure 5C:
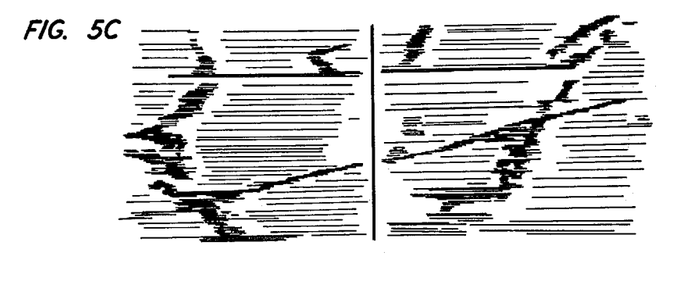

As heretofore noted, deformities may appear in the plastic coating during the application process. FIG. 5A illustrates the cross-sectional area of such a deformed fiber. FIGS. 5B and 5C show the respective backscattered light patterns generated in response to the two mutually perpendicular light beams incident upon this section of the fiber. No distinct intensity peaks can be noted in FIGS. 5B and 5C. Therefore, if such a pattern is perceived on either one or both of the observation screens 206 and 209, the location of a nonuniformity in the coating is determined.

Figure 6A:
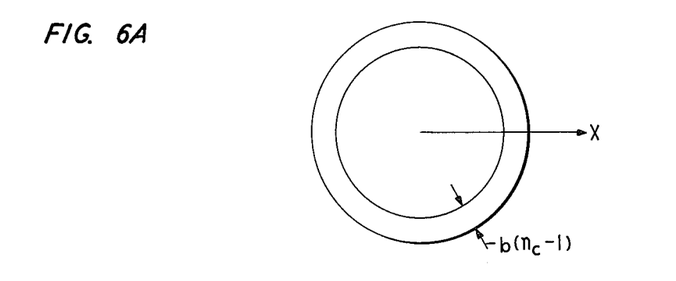
FIG. 6A is a cross-sectional view of a plastic coated fiber in which the coating has a predetermined thickness.
Figure 6B:
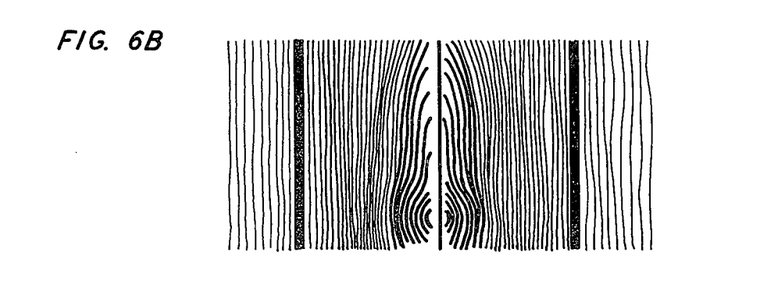
FIGS. 6B and 6C are the backscattered light patterns generated in response to light beams incident upon the fiber of FIG. 6A.
Figure 6C:
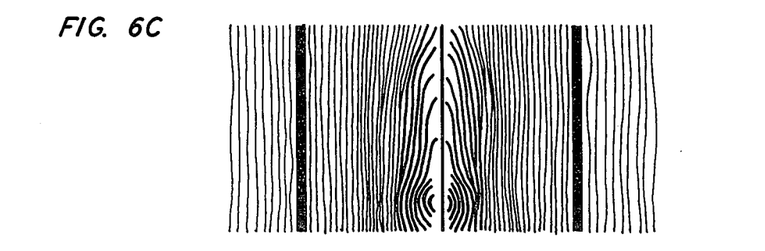

As heretofore described, when the radius of the coated fiber $a$ is less than or equal to $n_cb$, only one pair of intensity peaks is present in the backscattered light patterns. FIG. 6A illustrates a cross-sectional area of a concentric coated fiber in which $a$ is equal to $n_cb$. FIGS. 6B and 6C show the mutually perpendicular backscattered light patterns. As can be noted, only one pair of intensity peaks is present in each pattern, the end pair of intensity peaks having disappeared.

Figure 7:
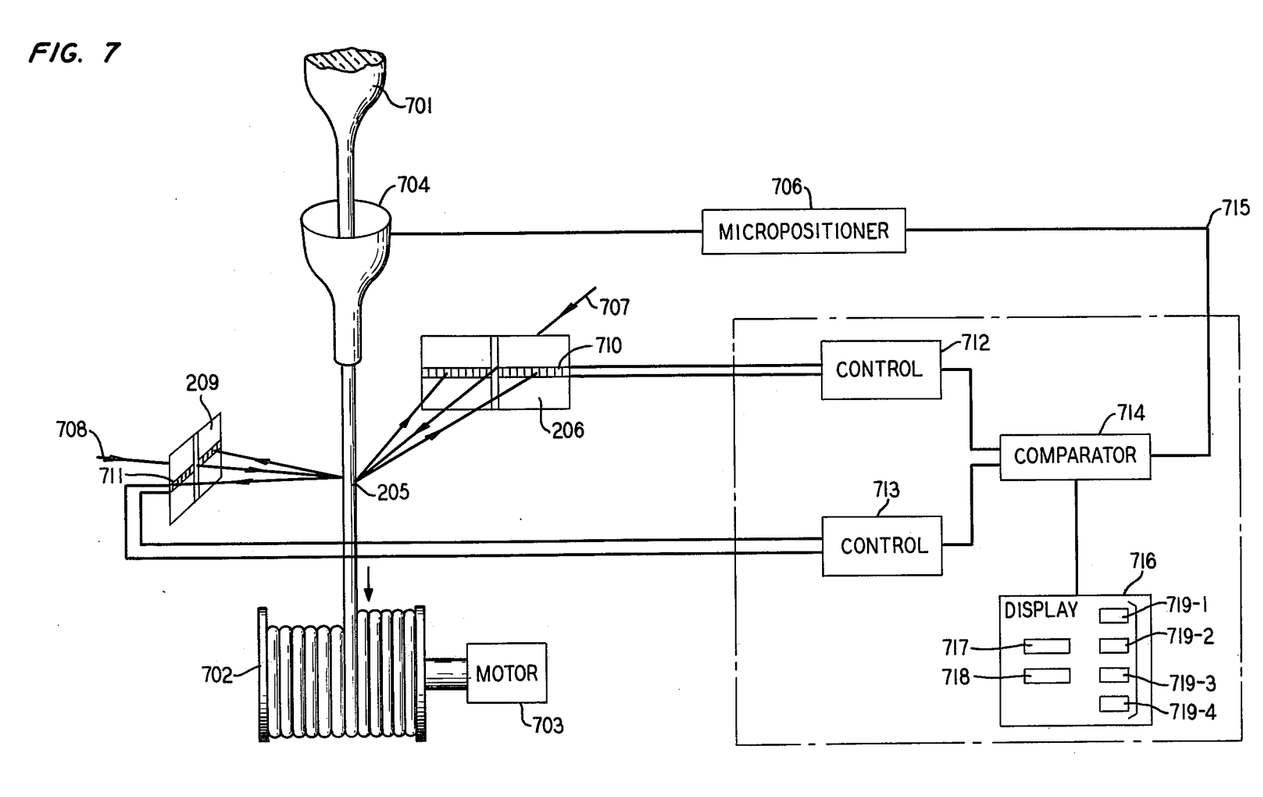
FIG. 7 shows apparatus which automatically controls the extrusion process by employing the monitoring technique of the present invention.

FIG. 7 illustrates a system which automatically compares the mutually perpendicular backscattered light patterns and generates a signal that controls the coating application process. Similar numerical designations are given to those elements in FIG. 7 that are also represented in FIG. 2. As the optical fiber 205 is drawn from a preform 701 onto a rotating drum 702, the latter being controlled by a motor 703, an applicator 704 which surrounds the fiber as it is being drawn, applies a plastic coating around the fiber. The position of applicator 704 around the fiber 105 is controlled by a micropositioner 706. As described immediately hereinbelow, micropositioner 706 is responsive to an electrical signal which is derived by comparing the backscattered light patterns generated in response to the two mutually orthogonal light beams incident upon the coated fiber. Light beam 707 passes through a slit in observation screen 206 and light beam 708 passes through a slit in observation screen 209 so that each beam impinges upon a section of the fiber 205 as it is pulled onto drum 702. As was described in detail, each incident beam is refracted and reflected by the plastic coated fiber to produce backscattered light patterns on observation screens 206 and 209. A scanning diode matrix 710 is disposed on observation screen 206 and scanning diode matrix 711 is disposed on observation screen 209. Scanning diode matrices 710 and 711 may be any one of a plurality of commercially available diode matrices such as one manufactured by the Reticon Corp. A control unit 712 is connected to scanning diode matrix 710 and a control unit 713 is connected to diode matrix 711. Control units 712 and 713, such as Reticon Controllers designed for interaction with the Reticon scanning diode matrices, convert the backscattered light patterns incident upon the respective matrices into electrical signals which have maxima and minima related to the light intensity maximas and minimas in the backscattered light patterns.

Figure 3D:
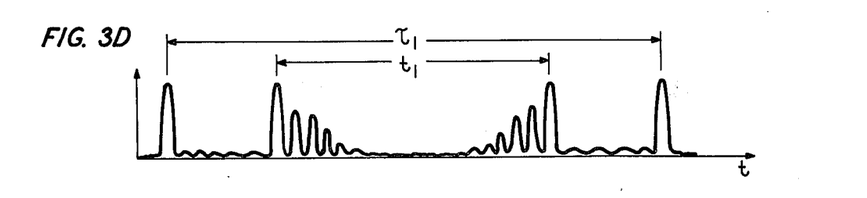
FIGS. 3D and 3E show the electrical signals generated by the backscattered light patterns in FIGS. 3B and 3C, respectively.
Figure 3E:
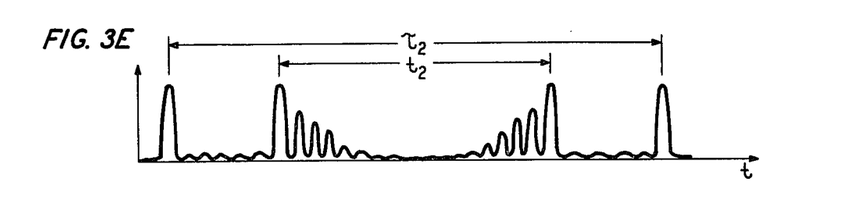
Figure 4D:
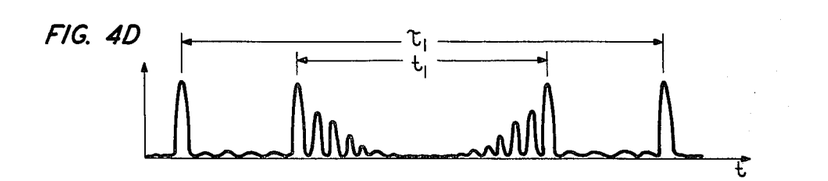
FIGS. 4D and 4E show the electrical signals generated from the backscattered light patterns in FIGS. 4B and 4C, respectively.
Figure 4E:
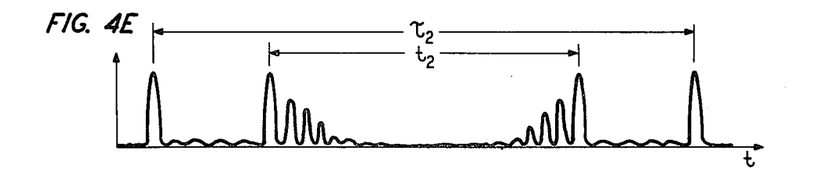

The outputs of control units 712 and 713 are connected to a comparator 714. A Hewlett-Packard 5300 Measurement Set coupled to a Hewlett-Packard 9825 Programmable Calculator can be used as comparator 714. Comparator 714 locates the maxima and minima of the electrical signals generated by control units 712 and 713. FIGS. 3D and 3E illustrate the electrical signals generated by control units 712 and 713 in response to the backscattered light patterns of FIGS. 3B and 3C, respectively, for the concentrically coated fiber of FIG. 3A. After locating the signal maximas, comparator 714 measures the time intervals between corresponding peaks in each signal, $t_1$ $t_2$, $\tau_1$ and $\tau_2$. Differences $t_1 - t_2$ and $\tau_1 - \tau_2$ are then automatically calculated. These differences are approximately zero for a concentrically coated fiber. When the fiber and coating are nonconcentric, such as the fiber illustrated in FIG. 4A, $t_1 - t_2$ and $\tau_1 - \tau_2$, determined from the electrical signals illustrated in FIGS. 4D and 4E, are nonzero. Comparator 714 generates a signal on lead 715 to control micropositioner 706 which, in turn, repositions applicator 704 to correct for the misalignment.

Figure 5D:
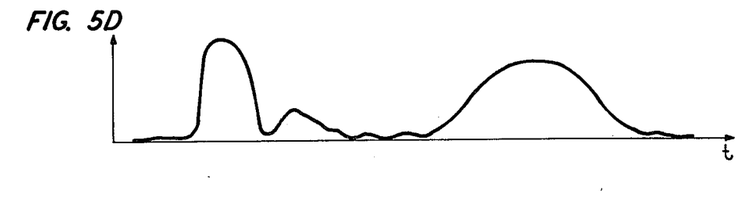
FIGS. 5D and 5E are the electrical signals generated from the backscattered light patterns in FIGS. 5B and 5C, respectively.
Figure 5E:
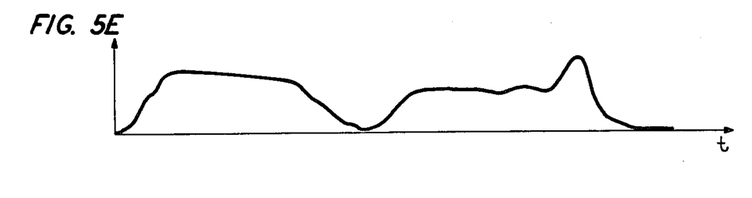

Comparator 714 is also connected to a display unit 716 such as Hewlett-Packard Interactive Display Terminal 2640. Display unit 716 includes two digital readouts 717 and 718 and four word readouts 719-1 through 719-4. As the fiber is drawn, readout 717 provides a continuous indication of $t_1 - t_2$ and readout 718 provides a continuous indication of $\tau_1 - \tau_2$. When the plastic coating is deformed, such as illustrated in FIG. 5A, the electrical signals derived from the backscattered patterns in FIG. 5B and FIG. 5C, have no defined intensity peaks, as can be noted in FIGS. 5D and 5E, respectively. In response to such signals at the outputs of control units 712 and 713, display unit 716 indicates unique codes on readouts 717 and 718 (e.g. 999) so that an operator monitoring the application process can readily note a coating deformation. The application process can thus be halted to correct the condition causing the deformity.

Figure 6D:
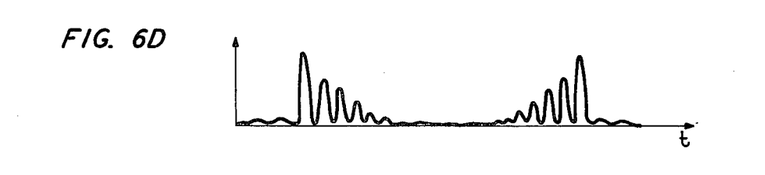
FIGS. 6D and 6E are the electrical signals generated in response to the backscattered light patterns in FIGS. 6B and 6C, respectively.
Figure 6E:
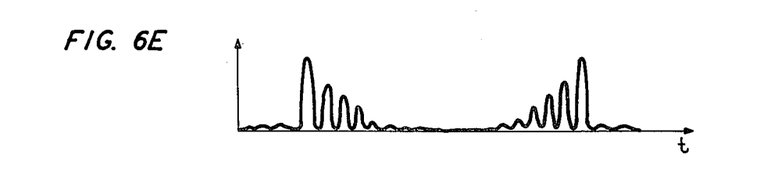

As heretofore noted, by monitoring the backscattered light patterns for the disappearance of the intensity peaks caused by the refraction and reflection of the incident rays that traverse only the coating, the thickness of the coating can be uniformly maintained at $b(n_{c-1})$, where $b$ and $n_c$ are previously defined. Comparator 714, in addition to noting the location of the intensity peaks in the electrical signals generated by control units 712 and 713, also provides an indication of the disappearance of the spatially extreme intensity peaks. FIGS. 6D and 6E show the electrical signals at the outputs of control units 712 and 713 when the coating is adjusted to the aforenoted thickness. Accordingly, word readouts 719-1 and 719-2 indicate the presence and absence of the two extreme intensity peaks in the backscattered pattern which falls on diode matrix 710, and word readouts 719-3 and 719-4 indicate the presence and absence of the two extreme intensity peaks in the backscattered pattern falling on diode matrix 711. As the fiber is being coated, the thickness of the coated fiber is maintained at $b(n_{c-1})$ by controlling the flow of coating material by applicator 704 onto the fiber until word readouts 719-1 through 719-4 each just indicate the disappearance of an extreme intensity peak. An operator can thus maintain this thickness uniformly by monitoring word readouts 719-1 through 719-4.

Various modifications of this invention can be made without departing from the spirit and scope of the invention. For example, a quasi-monochromatic light source such as a light emitting diode can be used in place of the monochromatic laser beam in the embodiment described hereinabove. Vidicon scanning techniques can also be used to monitor the backscattered light patterns. Furthermore, although described in connection with the monitoring of the properties of a plastic coating on an optical fiber, the present invention can be used to monitor the properites of any substantially transparent coating on any relatively transparent dielectric rod, or combination of rods.

The above-described arrangement is illustrative of the application and principles of the invention. Other embodiments may be devised by those skilled in the art without departing from the spirit and scope of the invention.

What is claimed is:

1. A method for monitoring the properties of a coating on a coated optical fiber, said coating being substantially transparent, comprising the steps of:
   illuminating said coated fiber with a beam of light incident to a cross-sectional axis of said fiber at a first angle;
   illuminating said fiber with a beam of light incident to said cross-sectional axis at a second angle;
   observing the first backscattered light pattern generated by said beam incident to said coated fiber at said first angle;
   observing the backscattered light pattern generated by said beam incident to said coated fiber at said second angle;
   comparing the spatial location of at least one intensity maxima in the first backscattered light pattern with the spatial location of a corresponding intensity maxima in the second backscattered light pattern; and
   determining the concentricity of said fiber within said coating from said comparison.

2. A method according to claim 1 wherein the difference between said first angle and said second angle is 90°.

3. A method for controlling an applicator which applies a coating onto an optical fiber, said coating being substantially transparent, comprising the steps of:
   illuminating the fiber onto which the coating has been applied with a beam of light incident to a cross-sectional axis of said fiber at a first angle;
   illuminating the coated fiber with a beam of light incident to said cross-sectional axis at a second angle;
   converting the first backscattered light pattern generated in response to said beam of light incident to said fiber at said first angle into a first electrical signal whose intensity variations, as a function of time, correspond to the spatial light intensity variations in said first backscattered light pattern;
   converting the second backscattered light pattern generated in response to said beam of light incident to said fiber at said second angle into a second electrical signal whose intensity variations, as a function of time, correspond to the spatial light intensity variations in said second backscattered light pattern;
   comparing the time differences between a predetermined pair of intensity maximas in said first electrical signal and a corresponding pair of intensity maximas in said second electrical signal; and
   generating a signal for adjusting the position of said applicator in response to said comparison.

4. The method according to claim 3 wherein the difference between said first angle and said second angle is 90°.

5. A method for monitoring the properties of a coating on a coated optical fiber, said coating being substantially transparent, comprising the steps of:
   illuminating said coated fiber with a first beam of light from a narrowband source:
   illuminating said coated fiber with a second beam of light from said narrowband source;
   comparing the spatial positions of the intensity maximas in the backscattered light patterns generated by said first beam and the spatial positions of the intensity maximas in the backscattered light patterns generated by said second beam; and
   determining the concentricity of said fiber within said coating from said comparison.

6. The method according to claim 5 wherein said second beam is perpendicular to said first beam, and said narrowband source is a CW laser.

7. A method for maintaining the thickness of a coating on a coated optical fiber at $b(n_{c-1})$ where $b$ is the radius of the optical fiber and $n_c$ is the index of refraction of the coating material, said coating being substantially transparent, comprising the steps of:
   illuminating said coated fiber with a beam of light from a narrowband source; and
   adjusting the flow of the coating material onto said optical fiber until the end pair of intensity peaks disappear from the backscattered light pattern generated by said beam of light.

8. The method according to claim 7 wherein said narrowband source is a CW laser.

9. A method for monitoring the properties of a coating on a substantially transparent dielectric rod, said coating also being substantially transparent, comprising the steps of:
   illuminating the coated rod with a beam of light incident to a cross-sectional axis of said rod at a first angle;
   illuminating the coated rod with a beam of light incident to said cross-sectional axis at a second angle;
   observing the first backscattered light pattern generated by said beam incident to the coated rod at said first angle;
   observing the backscattered light pattern generated by said beam incident to the coated rod at said second angle;
   comparing the spatial location of at least one intensity maxima in the first backscattered light pattern with the spatial location of a corresponding intensity maxima in the second backscattered light pattern; and
   determining the concentricity of said rod within said coating from said comparison.

10. The method according to claim 9 wherein the difference between said first angle and said second angle is 90°.

* * * * *